US008541224B2

(12) United States Patent
Bates et al.

(10) Patent No.: US 8,541,224 B2

(45) Date of Patent: Sep. 24, 2013

(54) **SERUM-FREE GROWTH MEDIUM FOR *ACHOLEPLASMA LAIDLAWII* AND METHODS FOR RETENTION TESTING STERILIZING GRADE FILTERS**

(71) Applicant: EMD Millipore Corporation, Billerica, MA (US)

(72) Inventors: Shawn Bates, Boston, MA (US); Kerry Roche Lentine, Tyngsboro, MA (US); Nada Bsat, Bedford, MA (US)

(73) Assignee: EMD Millipore Corporation, Billerica, MA (US)

(*) Notice: Subject to any disclaimer, the term of this patent is extended or adjusted under 35 U.S.C. 154(b) by 0 days.

(21) Appl. No.: 13/732,870

(22) Filed: Jan. 2, 2013

(65) Prior Publication Data

US 2013/0130356 A1 May 23, 2013

Related U.S. Application Data

(62) Division of application No. 12/675,318, filed as application No. PCT/US2008/009265 on Jul. 30, 2008, now Pat. No. 8,361,741.

(60) Provisional application No. 60/966,726, filed on Aug. 29, 2007.

(51) Int. Cl.

| | |
|---|---|
| ***C12N 1/20*** | (2006.01) |
| ***C12Q 1/02*** | (2006.01) |
| ***C12Q 1/22*** | (2006.01) |

(52) U.S. Cl.

USPC .......... 435/253.6; 435/29; 435/31; 435/252.1

(58) Field of Classification Search

USPC ........................................................ 435/252.1

See application file for complete search history.

(56) References Cited

U.S. PATENT DOCUMENTS

| | | | |
|---|---|---|---|
| 5,045,454 | A | 9/1991 | Bertheussen |
| 8,361,741 | B2 | 1/2013 | Bates et al. |
| 2007/0092961 | A1 | 4/2007 | Vargas |

FOREIGN PATENT DOCUMENTS

| | | | |
|---|---|---|---|
| WO | WO 2004/016341 A2 | 2/2004 | |
| WO | WO 2007/039069 A1 | 4/2007 | |

OTHER PUBLICATIONS

Raccach et al. Applied Microbiology, 1975, 30(2), 167-171.*

Jarhede et al. Methods in Molecular Biology, 1998, vol. 104, pp. 247-258.*

Jarhede et al. Microbiology. 1995, vol. 141, pp. 2071-2079.*

Low I.E. Applied Microbiology. 1974, vol. 27, No. 6, pp. 1046-1052.*

McCoy et al. International Journal of Systematic Bacteriology. 1984, vol. 34, No. 1, pp. 11-15.*

Hayflick L. "Tissues Cultures and Mycoplasmas". Texas Report on Biology and Medicine; 1965, 23:285-301.*

"PPLO Media (Mycoplasma Media) PPLO Agar (Mycoplasma Agar Base) PPLO Broth (Mycoplasma Broth Base) Mycoplasma Broth Base (Frey) Mycoplasma Supplement Mycoplasma Enrichment w/o Penicillin", *PPLO Media*, pp. 425-428 (Mar. 3, 2005). Retrieved from URL http://www.bd.com/ds/technicalCenter/inserts/PPLO_Media_Mycoplasma_Media.pdf.

Abu-Amero, K. K., et al., "Nisin Resistance Distinguishes *Mycoplasma* spp. from *Acholeplasma* spp. and Provides a Basis for Selective Growth Media", *Applied and Environmental Microbiology*, 62(9): 3107-3111 (Sep. 1996).

Albers, A. C., et al., "Simple Method for Quantitation of Viable Mycoplasmas", *Applied and Environmental Microbiology*, 43(4): 958-960 (Apr. 1982).

Beard, P., et al., "Cleavage of Circular, Superhelical Simian Virus 40 DNA to a Linear Duplex by $S_1$ Nuclease", *Journal of Virology*, 12(6): 1303-1313 (Dec. 1973).

Bhakoo, M., and McElhaney , R. N., "The Effect of Variations in Growth Temperature, Fatty Acid Composition and Cholesterol Content on the Lipid Polar Head-group Composition of *Acholeplasma laidlawii* B Membranes," *Biochimica et Biophysica Acta*, 945: 307-314 (1988).

Brough, H., et al., "Performance of a Novel Viresolve NFR Virus Filter", *Biotechnology Progress, American Institute of Chemical Engineers*, 18(4): 782-795 (2002).

Dussurget, O., et al., "Rapid, Sensitive PCR-Based Detection of Mycoplasmas in Simulated Samples of Animal Sera", *Applied and Environmental Microbiology*, 60(3): 953-959 (Mar. 1994).

Edman, M., et al., "Structural Features of Glycosyltransferases Synthesizing Major Bilayer and Nonbilayer-prone Membrane Lipids in *Acholeplasma laidlawii* and *Streptococcus pneumoniae", The Journal of Biological Chemistry*, 278(10): 8420-8428 (Mar. 2003).

Eriksson, P-O., et al., "Order and Dynamics in Mixtures of Membrane Glucolipids from *Acholeplasma laidlawii* Studied by $^2$H NMR", *Department of Physical Chemistry and Department of Biochemistry*, 30(20): 4916-4924 (1991).

Friis, N. F., "Some Recommendations Concerning Primary Isolation of *Mycoplasma suipneumoniae* and *Mycoplasma flocculare," Nord. Vet-Med.*, 27: 337-339 (1975).

Griffiths, M. W., et al., "Rapid Methods for Testing the Efficacy of Sterilization-Grade Filter Membranes", *Applied and Environmental Microbiology*, 66(8): 3432-3437 (Aug. 2000).

Hayflick, L., "Tissue Cultures and Mycoplasmas", *Texas Report on Biology and Medicine*, 23: 285-301 (Jun. 1965).

(Continued)

*Primary Examiner* — Vera Afremova

(74) *Attorney, Agent, or Firm* — Hamilton, Brook, Smith & Reynolds P.C.

(57) ABSTRACT

A method for retention testing sterilizing grade filters comprises: a) providing a stock of *Acholeplasma laidlawii*; b) growing up the stock of *A. laidlawii* for about 24 hours or less in a single serum-free growth medium that supports cell growth to a high titer and yields a cellular morphology where the cells are small, deaggregated and spherical, thereby producing a bacterial culture; c) challenging a test filter by filtering the bacterial culture through the test filter at a known challenge level, thereby producing a filtrate downstream of the test filter; and d) detecting concentration of *A. laidlawii* in the filtrate. Serum-free growth media for cultivating or storing *A. laidlawii* are also described.

28 Claims, 11 Drawing Sheets

(56) References Cited

OTHER PUBLICATIONS

Pollack, D. J., et al., "Reduction of Benzyl Viologen Distinguishes Genera of the Class *Mollicutes", International Journal of Systematic Bacteriology*, 46(4): 881-884 (Oct. 1996).
Raccach, M., et al., "Survival of Frozen Mycoplasmas", *Applied Microbiology*, 30(2): 167-171 (Aug. 1975).
Razin, S., "The Mycoplasmas", *Microbiological Reviews*, 42(2): 414-470 (Jun. 1978).
Razin, S., et al., "Cholesterol Requirement of Mycoplasma", *Journal of Bacteriology*, 102(2): 306-310 (May 1970).
Razin, S., et al., "Molecular Biology and Pathogenicity of Mycoplasmas", *Microbiology and Molecular Biology Reviews*, 62(4): 1094-1156 (Dec. 1998).
Roche, K. L., et al., "Methods Used to Validate Microporous Membranes for the Removal of Mycoplasma", *BioPharm*, 5(3): 22-33 (Apr. 1992).
Rose, D. L., et al., "A Test for Measuring Growth Responses of Mollicutes to Serum and Polyoxyethylene Sorbitan", *International Journal of Systematic Bacteriology*, 43(3): 527-532 (Jul. 1993).
Schmitt, K., et al., "A safe and efficient method for elimination of cell culture mycoplasmas using ciprofloxacin", *Journal of Immunological Methods*, 109: 17-25 (1988).
Stemke, G. W., and Robertson, J.A., "The Growth Response of *Mycoplasma hyopneumoniae* and *Mycoplasma flocculare* Based Upon ATP-dependent Luminometry," *Veterinary Microbiology*, 24: 135-142 (1990).
Sundaram, S., et al., "Application of Membrane Filtration for Removal of Diminutive Bioburden Organisms in Pharmaceutical Products and Processes", *PDA Journal of Pharmaceutical Science & Technology*, 53(4): 186-201 (Jul. 1999).
Sundstöm, T. K., et al., "Plasmid transformation and replica filter plating of *Acholeplasma laidlawii", FEMS Microbiology Letters*, 72: 147-152 (1990).
Technical Centre, "13.12 Integrity Testing", Dominick Hunter, pp. 1-8. Retrieved from URL http://www.dominickh.co.uk/tech_Centre.asp?chapter=1§ion=13_Integrity-Testing_12. [Retrieved on Jul. 31, 2007].
Uphoff, C. C., et al., "Mycoplasma Contamination in Human Leukemia Cell Lines," *Journal of Immunological Methods*, 149: 43-53 (1992).
Voelker, L., et al., "Association of Lysogenic Bacteriophage MAV1 with Virulence of *Mycoplasma arthritidis", Infection and Immunity*, 63(10): 4016-4023 (Oct. 1995).
Wallbrandt, P., et al., "Identification and Analysis of the Genes Coding for the Putative Pyruvate Dehydrogenase Enzyme Complex in *Acholeplasma laidlawii", Journal of Bacteriology*, 174(4): 1388-1396 (Feb. 1992).
Watanabe, T., "Effects on Manganese on Growth of *Mycoplasma salivarium* and *Mycoplasma orale", Journal of Clinical Microbiology*, 32(5): 1343-1345 (May 1994).
Whitcomb, R.F., "Culture Media for Spiroplasmas," *Methods of Mycoplasmology*, 1: 147-158 (1983).
Jarhede, T. K., et al., "Expression of foreign genes and selection of promoter sequences in *Acholeplasma laidlawii", Microbiology*, 141: 2071-2079 (1995).
Jarhede, T. K., et al., "Expression of Foreign Genes in *Acholeplasma laidlawii", Methods in Molecular Biology*, 104: 247-258 (1998).
Keceli, S. A., et al., "Differential Inhibition of Mollicute Growth: an Approach to Development of Selective Media for Specific Mollicutes", *Applied and Environmental Microbiology*, 68(10): 5012-5016 (Oct. 2002).
Low, I. E., "Isolation of *Acholeplasma laidlawii* from Commercial, Serum-Free Tissue Culture Medium and Studies on Its Survival and Detection", *Applied Microbiology*, 27(6): 1046-1052 (Jun. 1974).
Madsen, R. E., et al., "The Importance of Pre-Use Integrity Testing in Sterilizing Filtration", *Pharmaceutical Technology*, pp. 1-4. Retrieved from URL http://www.pharmtech.com/pharmtech/content/printContentPopup.jsp?id=423945. [Retrieved on May 9, 2007].
McCoy, R. E., et al., "*Acholeplasma* forum, a New Species Isolated from Plants", *International Journal of Systematic Bacteriology*, 34(1): 11-15 (Jan. 1984).
Miles, R. J., et al., "Oxygen uptake and $H_2O_2$ production by fermentative *Mycoplasma* spp.", *J. Med. Microbiol.*, 34: 219-223 (1991).
Millipore "Bacterial Retention Testing for Validation of Sterilizing-Grade Membrane or Quantification of Bioburden Reduction" (2006).
Nagatomo, H., et al., "Survival of Mycoplasmas Inoculated in Horse Sera", *Journal of Veterinary and Medical Sciences*, 59(6): 487-90 (1997).
Notification Concerning Transmittal of Copy of International Preliminary Report on Patentability for International Application No. PCT/US2008/009265, Dated: Mar. 11, 2010.
Notification of Transmittal of the International Search Report and Written Opinion of the International Searching Authority from counterpart International Application No. PCT/US2008/009265, dated Jan. 28, 2009.
Okazaki, N., et al., "Some Observations on Mycoplasma-Cidal Activity of Horse Serum", *Journal of Veterinary and Medical Sciences*, 54(2): 359-361 (1992).
Pollack, D. J., et al., "Reduction of Benzyl Viologen Distinguishes Genera of the Class *Mollicules", International Journal of Systematic Bacteriology*, 46(4): 881-884 (Oct. 1996).

* cited by examiner

SERUM-FREE GROWTH MEDIUM FOR *ACHOLEPLASMA LAIDLAWII* AND METHODS FOR RETENTION TESTING STERILIZING GRADE FILTERS

RELATED APPLICATION

This application is a divisional of U.S. application Ser. No. 12/675,318, which is the U.S. National Stage Application of International Application No. PCT/US2008/009265 filed on Jul. 30, 2008, published in English, which claims the benefit of U.S. Provisional Application No. 60/966,726 filed on Aug. 29, 2007. The entire teachings of the above applications are incorporated by reference herein.

BACKGROUND OF THE INVENTION

*Acholeplasma laidlawii* (*A. laidlawii*; ATCC 23206) is a wall-less bacterium in the Mollicutes class. Contrary to *Mycoplasma*, which belong to a different taxonomic order and have high sterol content membranes and thus require sterol addition to the growth media, *A. laidlawii* does not require sterols. *Acholeplasma laidlawii* has many fatty acid modified membrane proteins. Since it cannot make the unsaturated fatty acids it needs, it has a requirement for branched chain fatty acids in the growth media. *Acholeplasma laidlawii* makes acid from carbohydrates and lowers the pH of the growth media. However, it is sensitive to low pH.

Owing to its small size and common contaminant status, *A. laidlawii* is used as a model mycoplasma for retention testing 0.1 μm rated sterilizing grade filters. Industry and most laboratories use (horse) serum-containing media to cultivate it. Many media variants exist, as there currently is no standard medium or retention test recommended by federal or industry regulators for such filters. The test format is based on the existing *Brevundimonas diminuta* (*B. diminuta*) test for 0.2 μm rated sterilizing grade filters. Thus far, there are no standards for the media and methods used to grow *A. laidlawii*. Without such standards, it is difficult to compare and evaluate the retention data, especially since the media components affect the organism size and number, which, in turn, affect retention capacity, in terms of logarithmic reduction value (LRV).

SUMMARY OF THE INVENTION

The present invention presents the discovery in *A. laidlawii* cultivation that a single serum-free growth medium can support cell growth to a high titer and yields a cellular morphology suitable for retention testing sterilizing grade filters, and discloses standards for media and methods used to grow *A. laidlawii* for retention testing sterilizing grade filters.

In one embodiment of the invention, a method for retention testing sterilizing grade filters comprises providing a stock of *A. laidlawii*, growing up the stock of *A. laidlawii* for about 24 hours or less (e.g., from about 18 to about 24 hours) in a single serum-free growth medium that supports cell growth to a high titer and yields a cellular morphology where the cells are small, deaggregated and spherical, thereby producing a bacterial culture, challenging a test filter by filtering the bacterial culture through the test filter at a known challenge level, thereby producing a filtrate downstream of the test filter, and detecting concentration of *A. laidlawii* in the filtrate. The stock of *A. laidlawii* can be a frozen stock. The stock of *A. laidlawii* can be frozen in a solution comprising the same serum-free growth medium that is used to grow up the stock. The serum-free growth medium can comprise one or more nutrients, bovine serum albumin (BSA), one or more pH stabilizers, glucose and one or more fatty acids. The bacterial culture can have a titer of at least $1\times10^9$ cfu/mL. The test filter can be a 0.1 μm rated test filter. Detecting concentration of *A. laidlawii* in the filtrate can use a growth medium.

In a second embodiment of the invention, a serum-free growth medium for cultivating or storing *A. laidlawii* comprises about 4% tryptose; about 0.4% BSA; about 0.5% Trizma base; about 0.7% glucose anhydrous; about 75 μM oleic acid; and about 75 μM palmitic acid. The serum-free growth medium can be in the form of a broth or it can be in the form of an agar, which would contain, for example, about 1.2% agar. In a preferred embodiment, the pH of the serum-free growth medium is adjusted to about 7.8.

In a third embodiment of the invention, a serum-free growth medium for cultivating or storing *A. laidlawii* comprises about 4% polypeptone; about 0.4% BSA; about 0.5% Trizma base; about 0.7% glucose anhydrous; about 75 μM oleic acid; and about 75 μM palmitic acid. The serum-free growth medium can be in the form of a broth or it can be in the form of an agar, which would contain, for example, about 1.2% agar. In a preferred embodiment, the pH of the serum-free growth medium is adjusted to about 7.8.

In a fourth embodiment of the invention, a serum-free growth medium for cultivating or storing *A. laidlawii* comprises about 2% *Mycoplasma* Broth Base; about 0.4% BSA; about 0.5% Trizma base; about 0.7% glucose anhydrous; about 75 μM oleic acid; and about 75 μM palmitic acid. The serum-free growth medium can be in the form of a broth or it can be in the form of an agar, which would contain, for example, about 1.2% agar. In a preferred embodiment, the pH of the serum-free growth medium is adjusted to about 7.8.

In the embodiments above, when agar is present, the serum-free growth medium can further comprise a chromogenic agent or dye, for example, triphenyl tetrazolium chloride (TTC), Dienes stain, or crystal violet. When used in a growth medium comprising agar, TTC is preferably used at a final concentration between about 0.001% and about 0.01%, Dienes stain is preferably used at a final concentration of about 0.1% or less, and crystal violet is preferably used at a final concentration of about 0.1% or less.

The present invention revolutionizes the method of retention testing sterilizing grade filters by significantly reducing the amount of time to prepare *A. laidlawii* cells suitable for retention testing, simplifying the preparation of growth medium, and increasing consistency of the tests. Other features and advantages of the present invention are apparent from the additional descriptions provided herein including the different examples. The provided examples illustrate different components and methodology useful in practicing the present invention. Based on the present disclosure the skilled artisan can identify and employ other components and methodology useful for practicing the present invention.

BRIEF DESCRIPTION OF THE DRAWINGS

The foregoing will be apparent from the following more particular description of example embodiments of the invention, as illustrated in the accompanying drawings. The drawings are not necessarily to scale, emphasis instead being placed upon illustrating embodiments of the present invention.

DETAILED DESCRIPTION OF THE INVENTION

Figure 1:
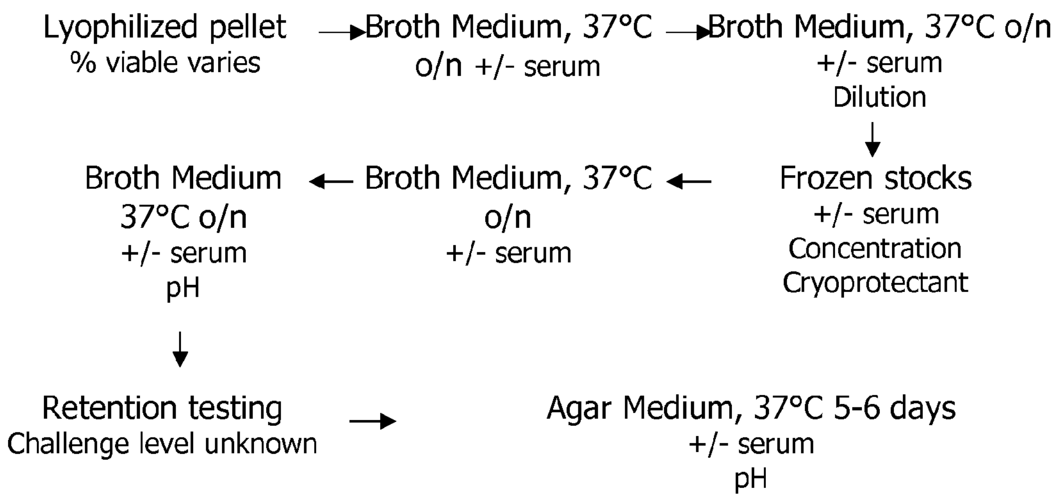
FIG. 1 is a flow-chart of a generalized procedure used in the industry for growing *A. laidlawii* for retention testing 0.1 μm rated sterilizing grade filters. Many steps include serum and can affect counts/viability and LRV.

The following abbreviations are used throughout the Specification:

BSA=bovine serum albumin
cfu=colony forming unit
CV=Coefficient of Variation
FDA=Food and Drug Administration
GHA=glucose hydrolysate agar
GHB=glucose hydrolysate broth
GMP=good manufacturing practice
HEPES=4-(2-hydroxyethyl)-1-piperazineethanesulfonic acid
LRV=logarithmic reduction value
MF=membrane filter
PES=polyethersulphone
PVDF=polyvinylidene fluoride
TTC=triphenyl tetrazolium chloride A description of example embodiments of the invention follows. The teachings of all patents, published applications and references cited herein are incorporated by reference herein in their entirety.

The present invention presents the discovery in *A. laidlawii* cultivation that a single serum-free growth medium can support cell growth to a high titer and yields a cellular morphology suitable for retention testing sterilizing grade filters, and discloses standards for media and methods used to grow *A. laidlawii* for retention testing sterilizing grade filters. The present invention revolutionizes the method of retention testing sterilizing grade filters by significantly reducing the amount of time to prepare *A. laidlawii* cells suitable for retention testing, simplifying the preparation of growth medium, and increasing consistency of the tests.

According to the invention, a method for retention testing sterilizing grade filters comprises providing a stock of *A. laidlawii*, growing up the stock of *A. laidlawii* for about 24 hours or less (e.g., from about 18 to about 24 hours) in a single serum-free growth medium that supports cell growth to a high titer and yields a cellular morphology where the cells are small, deaggregated and spherical, thereby producing a bacterial culture. As used herein, "cellular morphology" means any physical characteristics of the cells, e.g., size, shape and extent of aggregation, that can affect the result of a retention testing. Cellular morphology of *A. laidlawii* acceptable for retention testing 0.1 μm rated sterilizing grade filters include small size, homogeneity in size (narrow size distribution), spherical shape (length-to-width ratio near 1:1), and deaggregation (individual cells are separate from each other and do not form clusters). The serum-free growth medium of the invention is unique in that it is sufficient to support cell growth but provides an environment that stresses the bacteria. Under stress, the bacteria become spherical and deaggregated. This cellular morphology is conducive to retention testing. In addition, the absence of serum in the media minimizes fouling of the test membrane during filtration. This is beneficial because serum could artificially plug the test membrane leading to erroneous test results.

The cell culture is allowed to grow to an acceptable titer, which typically occurs in less than 24 hours using a single serum-free growth medium. The serum-free growth medium contains the necessary nutrients for cell growth to a high titer without sequential passaging in several different growth media, as can presently be done in the industry to first grow the cells and then to stress the cells to produce the appropriate cellular morphology for retention testing. In a preferred embodiment, the bacterial culture can have a titer of at least $1\times10^9$ cfu/mL.

After the cells have grown to acceptable titer and cellular morphology, retention testing is performed by challenging a test filter by filtering the bacterial culture through the test filter at a known challenge level, thereby producing a filtrate downstream of the test filter, and detecting concentration of *A. laidlawii* in the filtrate. Known methods for retention testing can be used and certain methods are described herein.

Sterile products need to be manufactured in sterile processes. Filtration is an effective method for sterilization, especially for heat liable pharmaceuticals and biologicals. The verification of filter performance has been identified as an important process in those applications where product sterilization or microbial bioburden reduction is required. The validation of the filtration is required by United States Food and Drug Administration (FDA). Retention testing is a destructive method for proving the capability of a filter product to meet its stated performance when it is installed in an application. This gives confidence to filter users that both before and after filtration processes the installed filter will achieve the required performance. As used herein, "retention testing" means a test method used to determine the bacterial retention characteristics of membrane filters for liquid filtration. Essential steps of a retention testing include providing sufficient amount of a challenge organism, challenging a membrane filter with the challenge organism by filtering the challenge organism through the membrane filter, thereby producing a filtrate downstream of the membrane filter, and detecting the concentration of the challenge organism in the filtrate. To fulfill the requirements of sterile filtration, a filter must be able to remove from the filtration stream all of the challenge organism and produce a sterile effluent.

Any suitable microorganism that is as small as or smaller than *B. diminuta* can be used as the challenge organism. This test method can be employed to evaluate any membrane filter system used for liquid sterilization. A membrane filter tested in a retention testing is also referred to herein as a test filter, or a test membrane. Membrane filters can be made of a number of materials well known to those skilled in the art. For example, DURAPORE® membrane is made of polyvinylidene fluoride (PVDF). (DURAPORE® is a registered trademark of Millipore Corporation, Billerica, Mass.) Other non-limiting examples of membrane material include polyethersulphone (PES).

The pharmaceutical industry specifies a sterilizing grade filter rated at 0.22 μm or less as one capable of producing a sterile filtrate when challenged with a solution containing sufficient *B. diminuta* organisms to give a concentration of $1\times10^7$ cfu/cm$^2$ of effective filtration area. As used herein, "sterilizing grade filters" means a filter which, when challenged with a suitable microorganism at a suitable minimum concentration, will produce a sterile effluent. With regard to FDA regulatory requirements, "sterilizing grade filters" means a filter, which, when challenged with the bacterium *B. diminuta*, at a minimum concentration of $10^7$ cfu per cm$^2$ of filter surface area, will produce a sterile effluent. The definition does not include a filter type or pore size recommendation. This must be determined by product/process specific bacterial retention testing. The amount of cells per effective filtration area used in a retention testing, also referred to herein as "challenge level," is defined as cfu of cells in a cell culture filtered through a test filter per cm$^2$ of the test filter through which the cell culture is filtered. Challenge level is a critical variable in retention testing. According to the regulations, challenges are conducted at a minimum level of $1.0\times10^7$ cfu/cm$^2$, which is considered worst-case for a bacterial challenge test. Although it is unlikely that a media or sera manufacturer would encounter such grossly contaminated material, the excessive challenge would ensure a level of safety over the actual bioburden present in the processor's upstream product.

There are a number of acceptable guidelines for retention testing and any can be used with the methods of this invention. For retention testing 0.2 μm rated sterilizing grade filters, the standard microorganism used is *B. diminuta*, and the standard minimum concentration used is $10^7$ cfu/cm$^2$ of filter surface area, as discussed in the FDA Guidance for Industry on Sterile Drugs Produced by Aseptic Processing. Parenteral Drug Association (PDA) Technical Report 26 is another industry guidance on filter validation. ASTM F838-05, "Standard Test Method for Determining Bacterial Retention of Membrane Filters Utilized for Liquid Filtration," published by ASTM International, is a recognized standard method for bacterial retention testing. The International Organization for Standardization (ISO) also has standard method for filter validation using *B. diminuta* (ISO 13408-2 Aseptic Processing). Other filter ratings are assessed similarly using different challenge organisms. Thus far, there are no specific standards for retention testing of membranes with pore ratings smaller than 0.2 μm. *Acholeplasma laidlawii* has been recommended as the challenge test microorganism for retention testing 0.1 μm rated sterilizing grade filters.

To provide a microorganism, e.g., *A. laidlawii*, in sufficient amount for retention testing, it is first grown up (also referred to herein as "cultivated") from a stock to a high titer in suitable growth media. A frozen stock is one way of keeping the viability of a biological strain over a long term (also referred to herein as "storing"). Other methods of storing a biological strain over a long time, e.g., storage in stab agar or slants, are well known in the art. The solution that is used to freeze the biological strain can comprise the same growth medium that is used to grow up the stock. It is useful to have a high titer so that devices with large surface area and devices with small surface area can be effectively challenged. The term "high titer" (also referred to herein as "high cell count"), as used herein, means a cell culture with a cell concentration (density), in terms of cfu/mL, suitable for retention testing, wherein the cell concentration is a result of cell growth during incubation, not of any process to concentrate the cells in the cell culture (e.g., by centrifugation). It should be noted that centrifugation can be used as a means to increase the cell concentration.

A generalized method used in the industry for growing *A. laidlawii* for retention testing 0.1 μm rated sterilizing grade filters is depicted in FIG. 1. Briefly, a lyophilized pellet of *A. laidlawii* is cultured in a broth medium overnight at 37° C., diluted and grown in a broth medium overnight again at 37° C. The resulting culture is concentrated, cryoprotectant added, and frozen to become frozen stocks. Two days before a retention test, a frozen stock is thawed and initially cultured in a nutrient-rich broth medium overnight at 37° C. This seed culture is used to inoculate a comparable nutrient-depleted broth medium. This inoculated culture is grown overnight at 37° C. *Acholeplasma laidlawii* cells cultured in this manner can exhibit acceptable cellular morphology (deaggregated and spherical) for use in a retention test, albeit they are used at an unknown challenge level. Some other procedures use a single medium to grow *A. laidlawii*. However, according to these procedures, *A. laidlawii* needs to be grown in a single medium for 72 to 96 hours in order to reach high titer. In addition, cell size, shape or degree of aggregation is never considered according to these procedures. Each of the procedures presently used in industry suffers many deficiencies, as will be discussed below.

Detecting the concentration of the challenge organism in the filtrate include any quantitative or qualitative analysis of the filtrate downstream of the test membrane in a retention test. This is the most critical part of any microbial retention test. The test must be designed so a single microorganism that penetrates the membrane filter and enters the downstream effluent will be detected. The methods can be classified as quantitative or qualitative. Quantitative methods include membrane filtration (MF), pour plating and spread plating. Qualitative methods include the direct inoculation technique. The growth media that are used to grow up a stock of a microorganism can also be used in each of these four methods to detect the microorganism downstream of a test membrane. In bacterial retention testing, quantitative methods are used for the assessment of the downstream effluent because one must calculate a log reduction value. The choice of method depends upon the expected concentration of cells to be detected.

When the expected concentration of cells to be detected is less than approximately 300 cfu, so that the colonies formed by the cells can be reliably counted in the absence of any dilution, the MF method is used. In the MF method, the entire filtrate is passed through a MF disc (usually a 0.45 μM mixed esters of cellulose substrate), which is then plated onto a suitable agar substrate and incubated under specified conditions. When the expected concentration of cells to be detected is greater than approximately 300 cfu, the spread plate or pour plate method is used. In these methods, a sample of effluent is serially diluted. In the case of the spread plate method, aliquots are applied to agar so as to allow an even distribution of colonies on the agar surface. In the case of the pour plate method, the diluted aliquots are mixed with molten, but tempered agar, then poured into a Petri dish. In the direct inoculation method, the entire filtrate is collected into a sterile flask that contains an appropriate concentrated broth growth medium. The flask is then incubated under specified conditions. Using the MF method enables the technician to evaluate 100% of the effluent and to enumerate the microbial colonies directly. The original microbial concentration present in the direct inoculation method cannot be precisely determined.

Several problems exist in the procedure used in the industry for growing *A. laidlawii* for retention testing 0.1 μM rated sterilizing grade filters. According to procedures used in the industry, *A. laidlawii* can be sequentially grown in two different growth media for over 48 hours or in a single medium for 72 to 96 hours, making the total time for preparation of *A. laidlawii* culture suitable for retention testing from two days to 96 hours depending upon the method. Several of the media used in the industry contains serum. While serum-containing media allow good growth of *A. laidlawii*, they are unreliable and inconsistent, primarily due to an inherent high source variability. Serum suppliers going out of business, stopping or delaying production and changing production procedure contribute to the unreliability and inconsistency of serum supply. Moreover, even if the suppliers maintain a steady production using consistent procedure, animals from which serum is produced (e.g., horses) differ, their serum constituents (e.g., protein and cholesterol) affected by diet, activity and illness, which may result in undesirable *Mycoplasma* and antibodies in the serum. Such variability can impact not only cell counts, but also cell size and surface properties (thus LRV). Cells cultured using serum-containing media tend to aggregate, are not homogeneous in size, both contributing to variations in LRV. Moreover, inconsistent counts delay product release as low or unreliable counts can disqualify test results that require a minimum bacterial challenge for release.

The present invention solves these problems by using a single serum-free growth medium in a single incubation step for growing up *A. laidlawii* that can produce an *A. laidlawii* culture with high titer and cellular morphology suitable for retention testing, thereby significantly shortening the incubation time and eliminating the unreliability and inconsistency related to serum-containing media. As used herein, “serum-free” means any composition that does not contain serum, and “a single serum-free growth medium” means that only one growth medium that does not contain serum is used in a single incubation step to grow up *A. laidlawii*, resulting in a cell titer and cellular morphology suitable to be used in retention testing. The serum-free growth medium can be formulated as a broth or into agar plates. A serum-free broth medium according to the present invention can grow up an *A. laidlawii* culture to acceptable cell titer and cellular morphology for retention testing in a single incubation step that takes about 24 hours or less.

In one embodiment, the serum-free growth medium comprises one or more nutrients, BSA, one or more pH stabilizers, glucose and one or more fatty acids. For example, the one or more nutrients are selected from the group consisting of peptone, *Mycoplasma* Broth Base, and a combination thereof. Suitable peptones for use in the serum-free groth medium include but are not limited to tryptose, polypeptone, proteose peptone, phytone, soytone, and combinations thereof. Suitable pH stabilizers include but are not limited to Tris, 4-(2-hydroxyethyl)-1-piperazineethanesulfonic acid (HEPES), and a combination thereof. Suitable fatty acids include but are not limited to oleic, palmitic, myristic acids, and combinations thereof.

In a preferred embodiment, the serum-free growth medium for cultivating or storing *A. laidlawii* comprises about 4% tryptose; about 0.4% BSA; about 0.5% Trizma base; about 0.7% glucose anhydrous; about 75 μM oleic acid; and about 75 μM palmitic acid. As discussed in detail below, this medium is also referred to as Medium C. This serum-free growth medium can be formulated in broth or agar, for example from about 1.0% to about 1.5% agar, with about 1.2% to about 1.5% being preferred. The pH of the serum-free growth medium is adjusted to between about 7.7 and about 8.4. In a preferred embodiment, the pH is adjusted to about 7.8.

In another embodiment of the invention, a serum-free growth medium for cultivating or storing *A. laidlawii* comprises about 4% polypeptone; about 0.4% BSA; about 0.5% Trizma base; about 0.7% glucose anhydrous; about 75 μM oleic acid; about 75 μM palmitic acid. This serum-free growth medium can be formulated in broth or agar, for example from about 1.0% to about 1.5% agar, with about 1.2% to about 1.5% being preferred. The pH of the serum-free growth medium is adjusted to between about 7.7 and about 8.4. In a preferred embodiment, the pH is adjusted to about 7.8.

In yet another embodiment of the invention, a serum-free growth medium for cultivating or storing *A. laidlawii* comprises about 2% *Mycoplasma* Broth Base; about 0.4% BSA; about 0.5% Trizma base; about 0.7% glucose anhydrous; about 75 μM oleic acid; about 75 μM palmitic acid. This serum-free growth medium can be formulated in broth or agar, for example from about 1.0% to about 1.5% agar, with about 1.2% to about 1.5% being preferred. The pH of the serum-free growth medium is adjusted to between about 7.7 and about 8.4. In a preferred embodiment, the pH is adjusted to about 7.8.

In the embodiments above, when agar is present, the serum-free growth medium can further comprise a chromogenic agent or dye, for example, triphenyl tetrazolium chloride (TTC), Dienes stain, or crystal violet. The chromogenic agent or dye can be mixed into the agar-containing medium during preparation of the medium, preferably before the medium solidifies, so that the chromogenic agent or dye is distributed evenly throughout the solidified agar-containing medium. Inclusion of a chromogenic agent or dye into the agar-containing medium is advantageous because colonies grown on such medium are stained with a color as they are formed during incubation, making the messy post-incubation staining step unnecessary. Enumeration of the colonies can be performed manually, by digital capture or by automated colony capture. Preferably, TTC is included into the agar-containing growth medium. TTC is a colorless agent when it is in the oxidized form, the form it is used when included in the medium. The reduced form of TTC is insoluble red triphenyl formazan. Once a microorganism such as *A. laidlawii* reduces TTC to formazan as it grows, the reaction is irreversible. The agar and membrane filters do not interact with TTC, therefore retain their neutral colors. The contrast between the neutral background and the red colonies allows for effective automated colony enumeration.

Formulation and preparation of these chromogenic agents and dyes are well known to those skilled in the art. When used in a growth medium comprising agar, TTC is preferably used at a final concentration between about 0.001% and about 0.01%, Dienes stain is preferably used at a final concentration of about 0.1% or less, and crystal violet is preferably used at a final concentration of about 0.1% or less.

The present invention is based in part on the discovery that *A. laidlawii* grew better (by 3 logs) in the absence of serum and other nutritional additives in Hayflick's base medium, compared to growth in complete Hayflick's medium.

To examine the effect of omission of serum in growth medium for *A. laidlawii*, effect of serum omission in growth medium on growth, cell size and retention of *A. laidlawii* was tested in both liquid and agar-containing media. It was surprisingly found that adding serum to either one of the two broth media used to grow up *A. laidlawii* to be used in retention testing decreased the final cell counts in FIG. 1 by ~2 logs, and another log was lost if both media contained serum. In the absence of serum, cells were more homogeneous in size, with the majority of the population in mid-higher 0.3 μm. In the presence of serum, the cells had an average size of ~0.3 μm.

To compare retention of *A. laidlawii* produced in serum-containing and serum-free growth media, DURAPORE® filter or membrane LRVs were obtained when tested using cells grown in media with and without serum. LRV, an important expression of retention efficiency, is calculated using the following formula:

$$LRV = \mathrm{Log}_{10}\frac{\text{Total Challenge in } cfu/\text{device}}{\text{Total Passage in } cfu/\text{device}}$$

wherein "device," as used herein, refers to the filter being tested. For a filter to be sterilizing, the total passage must be less than 1 cfu/device, and the LRV must be greater than $\mathrm{Log}_{10}$(Total Challenge in cfu/device).

It was found that when tested using cells grown in media with and without serum, DURAPORE® filter or membranes gave similar LRVs, indicating that *A. laidlawii* grown in serum-free growth medium have similar retention characteristics to those grown in serum-containing medium. In addition, it was found that serum-containing Media 78 agar plates were found not to be able to support good growth, compared to serum-free Media 78 agar plates. Furthermore, it was discovered that the cells grew very well in serum-free medium in less than 2 days, because cell counts decreased over 2 days of incubation unless the cells were diluted.

To examine the effect of pH in growth medium for *A. laidlawii*, serum-containing media buffered with HEPES were used to test the effect on growth of *A. laidlawii*. It was found that HEPES-buffered serum-containing media increased cell counts compared to serum-containing media without HEPES buffering.

In order to develop a serum-free medium for *A. laidlawii*, different combinations of a list of media ingredients at various concentrations were tested for their effect on growth, cell size and retention of *A. laidlawii*. The primary selection criteria were growth sustenance to high cell counts and good colony size. The secondary selection criterion was LRV, where the goal was to obtain values similar to those obtained with serum-containing media. It was found that fatty acids, glucose, high tryptose, BSA and proper pH adjustment all contributed to the improvement of cell counts and homogeneity of proper cell size. Higher tryptose in the medium even reduced the culturing time from 48 to 24 hours or less. One specific combination of media ingredients is listed in Table 1 and is referred to herein as Medium C.

TABLE 1

| Medium C liquid | | |
|---|---|---|
| Ingredient | Supplier/Catalog # | % or μM |
| Tryptose | Sigma/T2813 | 4% |
| BSA | Sigma/A6003 | 0.4% |
| Trizma base | Sigma/T6791 | 0.5% |
| Glucose•$H_2O$ | Fluka/49158 | 0.77%* |
| Oleic acid | Sigma/O1008 | 75 μM |
| Palmitic acid | Sigma/P0500 | 75 μM |

*Or 0.7% if anhydrous

In retention tests, *A. laidlawii* grown in Medium C gave DURAPORE® membrane and PES membrane LRVs similar to those when grown in serum-containing media.

Because the procedure used in the industry includes a step of freezing *A. laidlawii* in serum-containing medium and keeping the frozen stock at a temperature of −70° C. or lower (FIG. 1), the applicants investigated whether serum-free growth medium is suitable for freezing and keeping *A. laidlawii* at a temperature of −70° C. or lower (third criterion). It was found that Medium C was adequate for frozen stocks of *A. laidlawii* and could give −70° C. viability over time. Incorporation of glycerol in Medium C can improve viability during frozen storage over time.

The effect of different nutrients on the growth, size and LRV of *A. laidlawii* was further tested by replacing tryptose in Medium C with other nutrients. *Mycoplasma* Broth Base (Difco/211458) was found to be able to substitute tryptose and meet all three criteria discussed above. Various plant and animal hydrolysates (e.g., polypeptone, proteose peptone, phytone, and soytone) were selected and tested in growth promotion studies. Based on those studies, formulations that gave cell titers equal to or higher than the tryptose formulation were chosen and tested in a retention series using different membranes. For substitutes giving LRVs comparable to historically obtained values, they were further tested for run-to-run consistency. Tables 2 and 3 list two other specific examples of serum-free growth medium compositions of the present invention, referred to herein as GHA and GHB, respectively. *A. laidlawii* grown in the serum-free growth medium of the present invention can reach a titer higher than $1\times10^9$ cfu/mL.

TABLE 2

| Glucose Hydrolysate Agar (GHA) plates, pH adjusted to 7.8 | | |
|---|---|---|
| Ingredient | Supplier/Catalog # | % or μM |
| Mycoplasma Broth Base | Difco/211458 | 2% |
| BSA | Sigma/A6003 | 0.4% |
| Trizma base | Sigma/T6791 | 0.5% |
| Glucose•$H_2O$ | Fluka/49158 | 0.77%* |
| Oleic acid | Sigma/O1008 | 75 μM |
| Palmitic acid | Sigma/P0500 | 75 μM |
| Agar | Oxoid Remel/661132 | 1.2% |

*Or 0.7% if anhydrous

TABLE 3

| Glucose Hydrolysate Broth (GHB) | | |
|---|---|---|
| Ingredient | Supplier/Catalog # | % or μM |
| Polypeptone | BBL/211910 | 4% |
| BSA | Sigma/A6003 | 0.4% |
| Trizma base | Sigma/T6791 | 0.5% |
| Glucose•$H_2O$ | Fluka/49158 | 0.77%* |
| Oleic acid | Sigma/O1008 | 75 μM |
| Palmitic acid | Sigma/P0500 | 75 μM |

*Or 0.7% if anhydrous

EXAMPLE 1

Culture Titer

Figure 2:
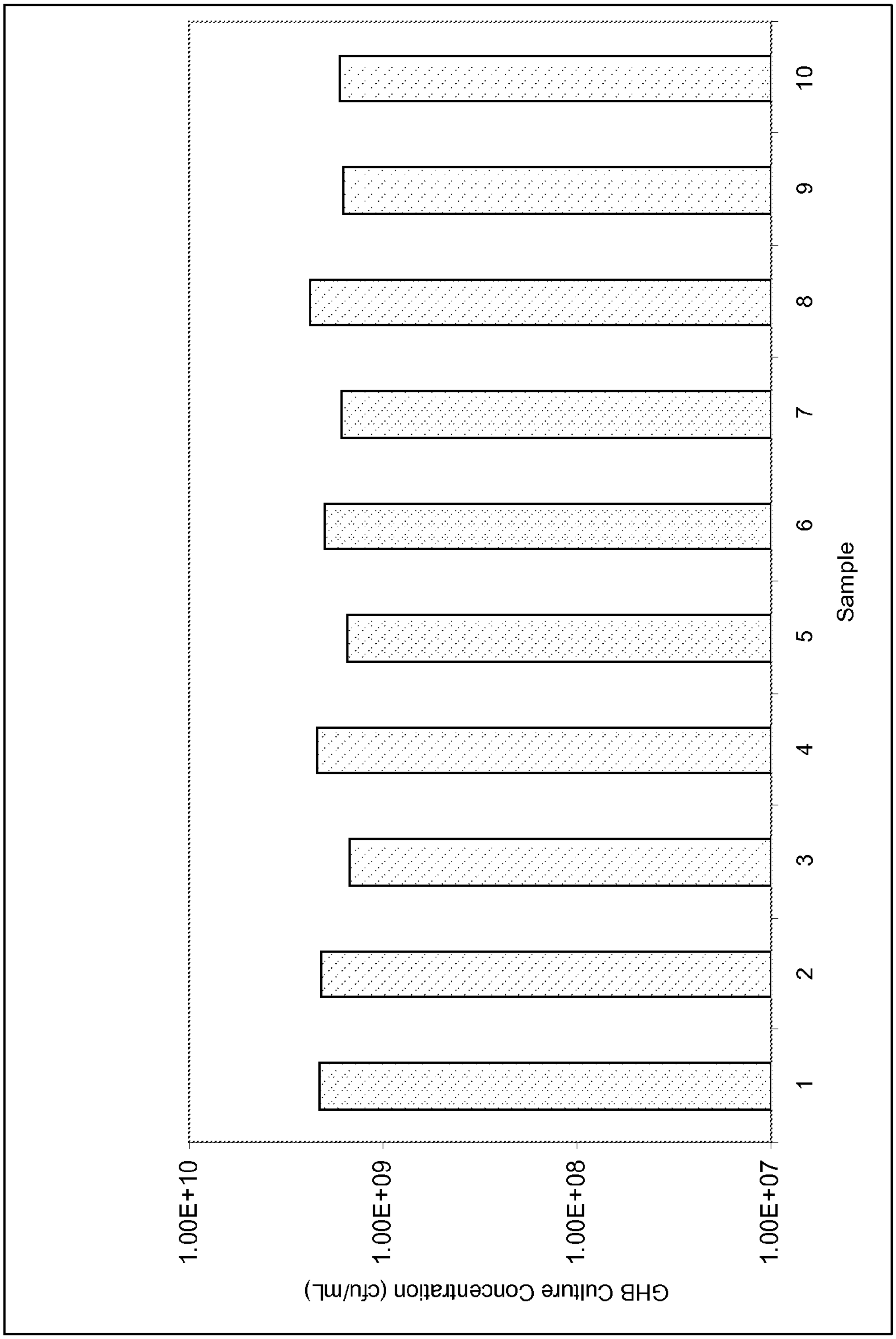
FIG. 2 is a bar graph showing cell concentration (colony forming units per milliliter; cfu/mL) obtained from cultures grown in a serum-free growth medium according to the present invention in 10 different samples.

To demonstrate that the culturing process using the serum-free growth medium of the present invention can produce *A. laidlawii* at a consistent concentration, two different analysts assessed the titer of *A. laidlawii* (ATCC 23206) cultivated in glucose hyrolysate using different lots of GHB and GHA on different days. FIG. 2 illustrates the culture titer (cfu/mL) of 10 samples cultivated in GHB and enumerated on GHA. The results demonstrate that the culturing process can produce *A. laidlawii* to a consistent concentration, with an average of $1.88\times10^9$ cfu/mL and a standard deviation of $3.18\times10^8$ cfu/mL.

EXAMPLE 2

Frozen Stock Titer

Figure 3A:
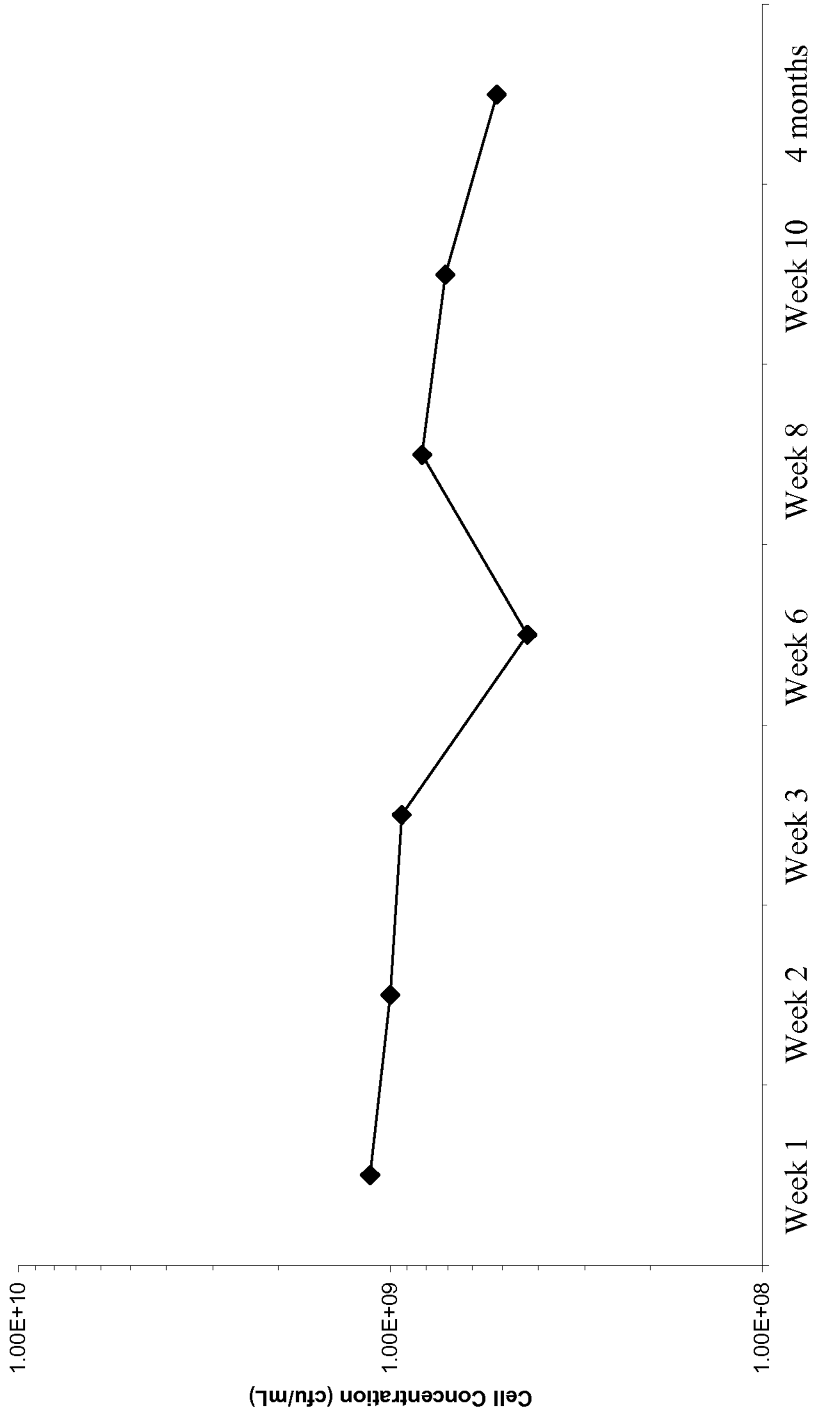
FIGS. 3A-C are graphs showing cell concentration (cfu/mL) obtained from frozen *A. laidlawii* stocks frozen in a serum-free growth medium according to the present invention and stored over time.
Figure 3B:
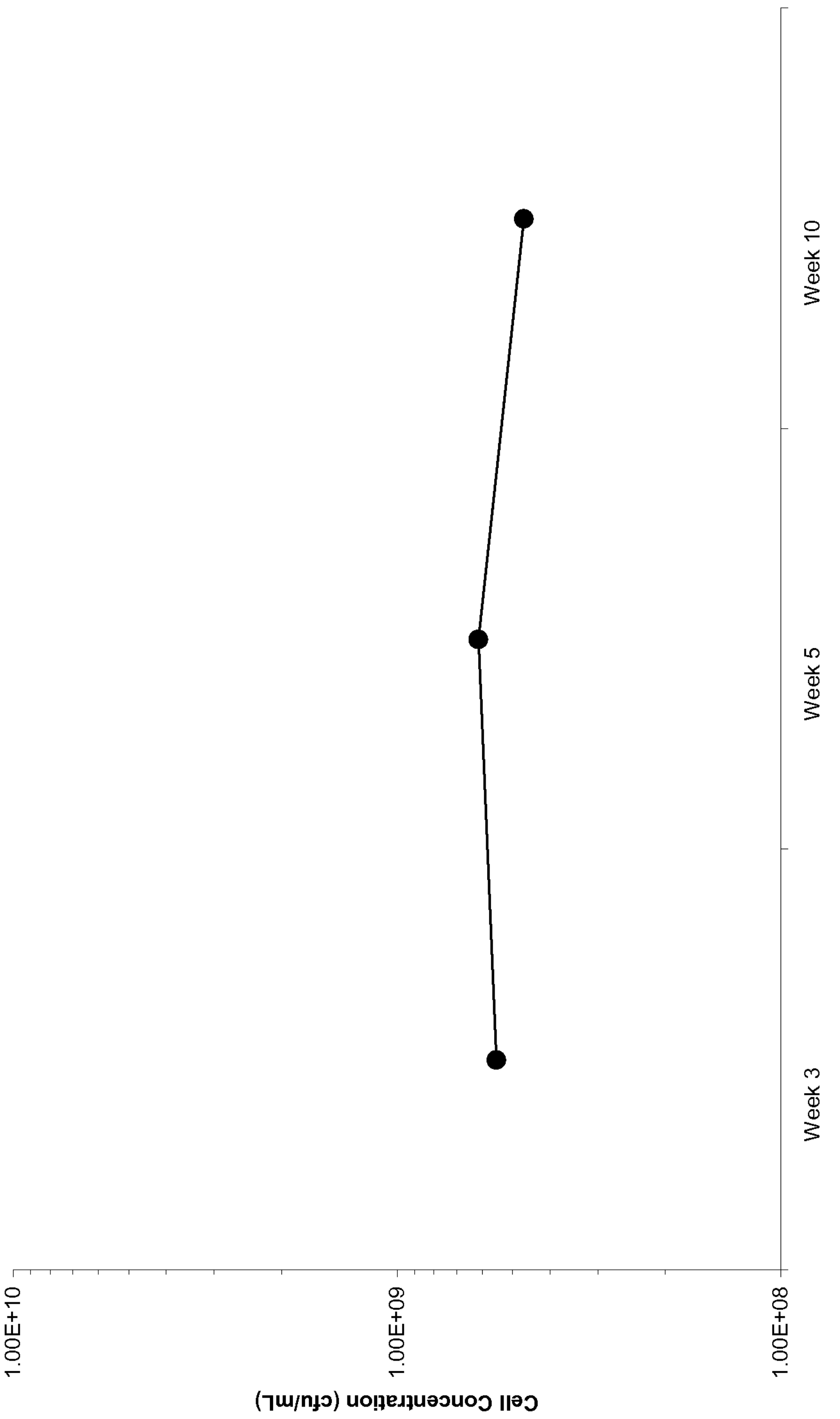
Figure 3C:
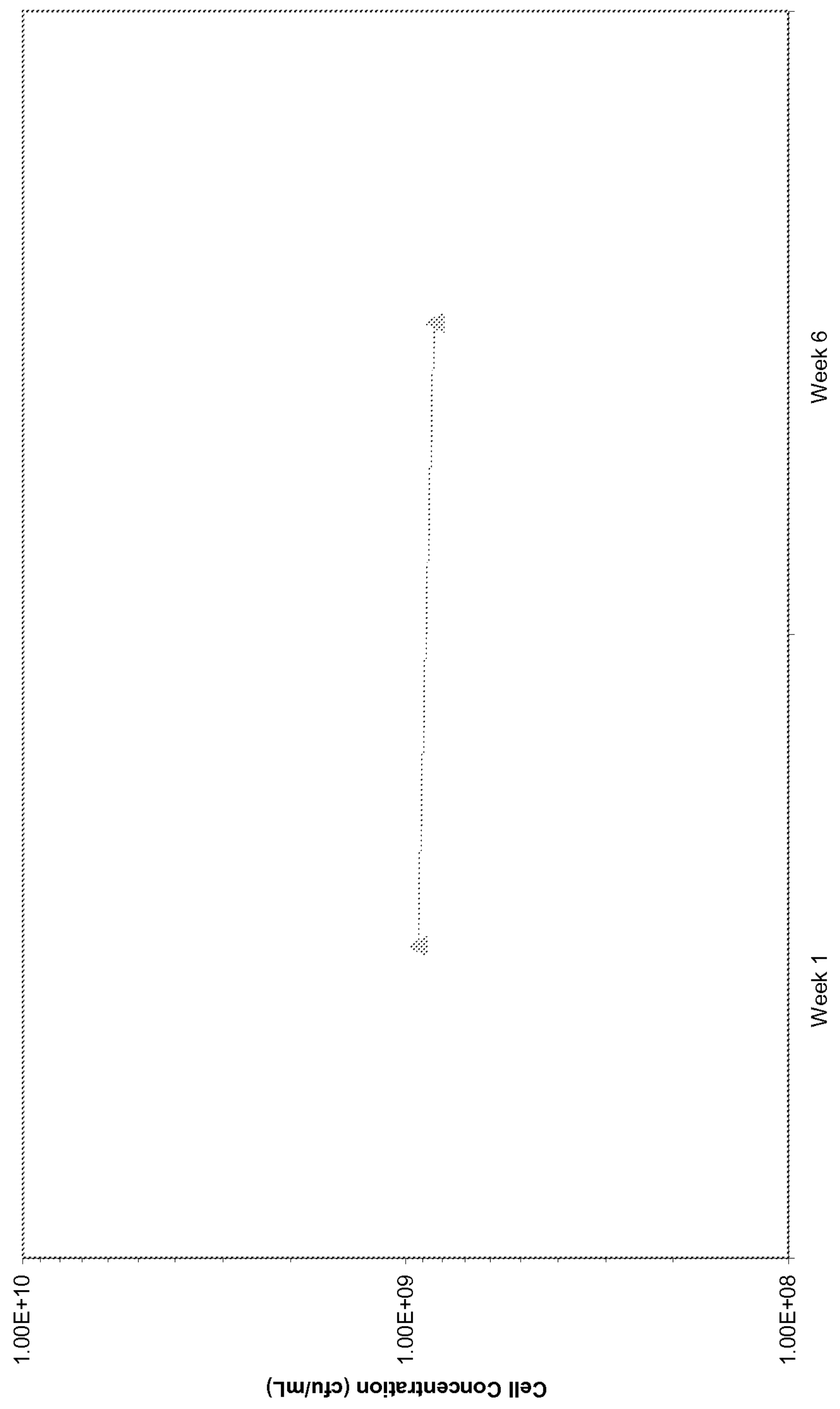

To monitor the titer of a frozen stock of *A. laidlawii* frozen in GHB over time, different frozen stocks were thawed and their titers enumerated via dilution, plating and incubation. This differs from the culture titer in Example 1, where the frozen stocks were thawed and then inoculated into GHB and incubated prior to enumeration via dilution and plating. FIGS. 3A-C illustrate the titer (cfu/mL) of different frozen stocks over time. The results demonstrate that a frozen stock can maintain a shelf life of up to four months without significant drop in titer. The results presented in FIGS. 3A-C and testing of frozen stocks frozen for longer periods can help establish a stocking schedule for *A. laidlawii.*

EXAMPLE 3

Recovery Assay

To demonstrate that GHA can reproducibly recover and enumerate *A. laidlawii* accurately and precisely over the applicable range, *A. laidlawii* recovery assays with presence/absence qualifications were performed. Briefly, *A. laidlawii* was grown in GHB for 18-24 h at 37° C., 7% $CO_2$. 0.2 mL of the resulting culture, which had a cell concentration of about $1.5\times10^9$ cfu/mL (see Example 1) was subject to a 1:100 serial dilution thereby producing a diluted culture of about $1.5\times10^3$ cells in 20 mL. 10 mL of the diluted sample was subject to a two-fold serial dilution. Both pour plates and MF plates using GHA were prepared in triplicates for the samples in the second dilution series. Samples of the second dilution series were assayed either by pour plate method or MF method using 0.22 μm DURAPORE® (GV) membrane. 0.22 μm GV membrane was used based on the data showing that such membrane improved recovery to greater than 90% versus pour plating when compared to less than 50% recovery using 0.2 μm mixed esters of cellulose (GS) membrane. Effluent was collected downstream of the assay filter into double strength GHB (GHB medium in which each ingredient has a concentration two times as shown in Table 3) which was then incubated at 37° C., 7% $CO_2$ for 7 days for the presence or absence of the test microorganism as evidenced by turbidity when compared to positive and negative controls. Assay membrane filters and pour plates were enumerated after incubation at 37° C., 7% CO2 for 4 days.

A comparison of pour plate recovery results to membrane assay filter recoveries showed that overall for all dilutions recovery is 114% with MF recovering equal to or better than spread plate.

All effluent downstream of assay filters exhibited no growth of the test microorganism as compared to positive and negative controls, indicating sterile effluent downstream of assay filter.

Figure 4:
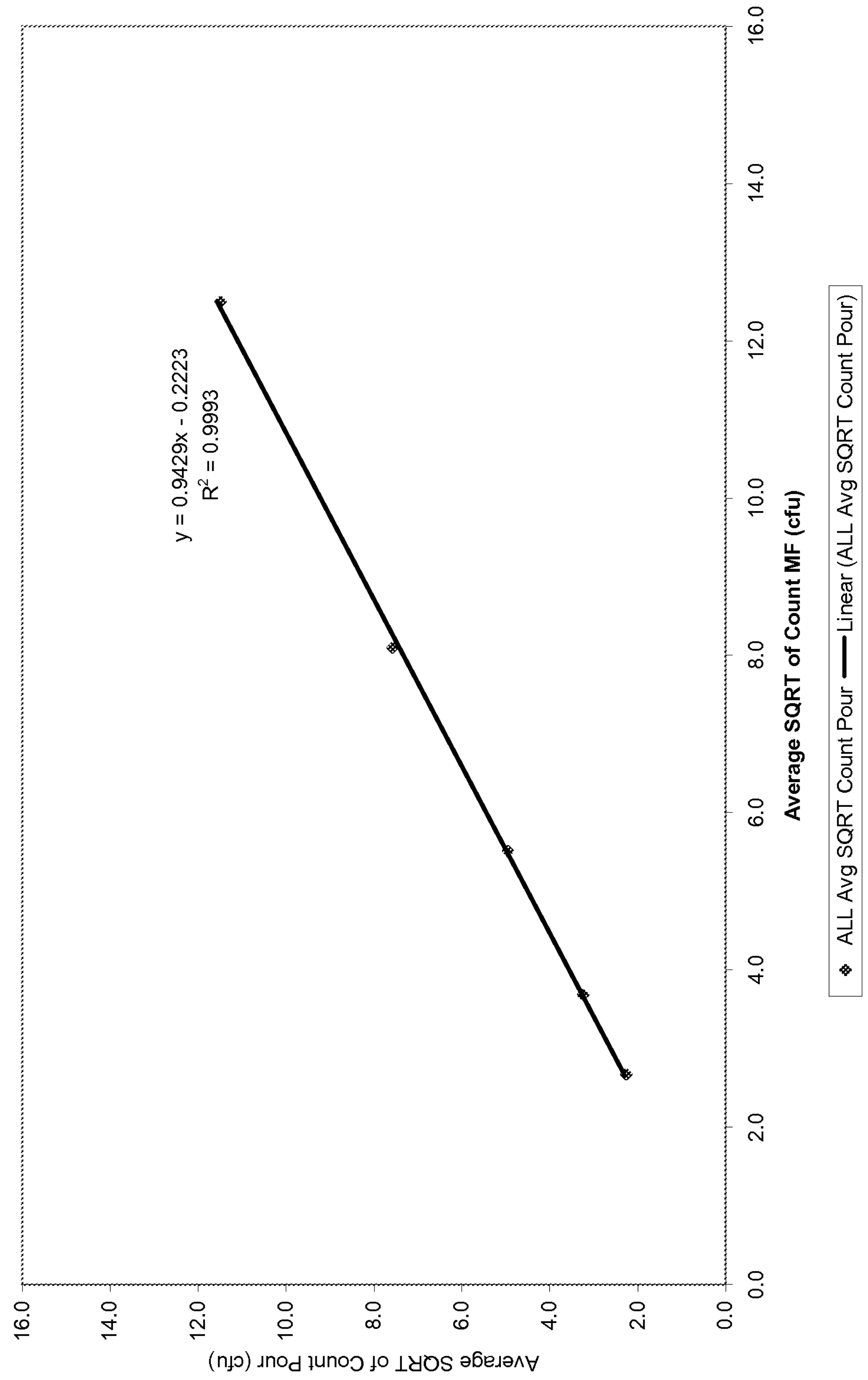
FIG. 4 is a graph showing the correlation between membrane filtration and pour plate methods in 10 separate tests containing triplicates of each dilution in the *A. laidlawii* recovery assay using serum-free growth medium according to the present invention.

Pour plates and membrane assay filters were found to recover organisms in a linear fashion, with an average correlation coefficient of 0.9815 and a standard deviation of 0.0177. FIG. 4 illustrates the correlation between membrane filtration and pour plate in 10 separate tests containing triplicates of each dilution.

The assay was found to be able to accurately and precisely detect a range of lower than 20 to higher than 300 cfu in a sample using both the pour plate and MF recovery techniques. As expected, % CV tended to increase as the cell concentration became smaller, but in no case was the % CV at 20 cfu greater than 35% using triplicate results from the same dilution, indicating high precision (repeatability) of the assay.

EXAMPLE 4

Growth Curve

Figure 5:
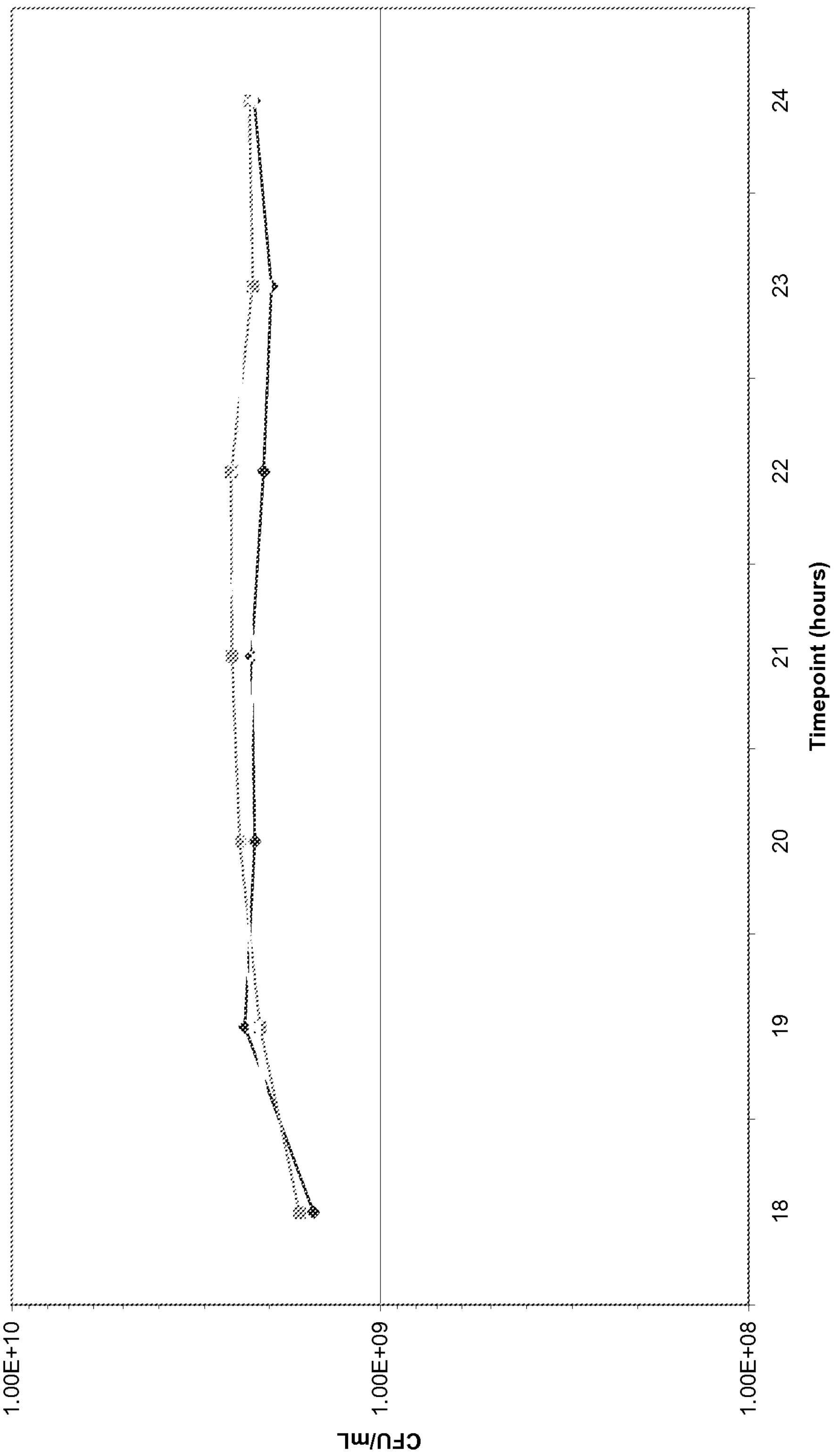
FIG. 5 is a graph showing growth curves of *A. laidlawii* grown for 18 to 24 hours in the serum-free growth medium according to the present invention.

To document the time at which the culture is used within the window at which no significant change to cell concentration occurs, three growth curve assays were performed on different days using different batches of GHB and GHA. Each GHB and GHA component was weighed, mixed and sterile filtered or autoclaved separately. Culturing and enumeration were performed as described in Example 3. FIG. 5 illustrates the growth curves between 18 and 24 hours of incubation of *A. laidlawii* ATCC 23206 lot #3895225 in GHB, obtained in the three separate experiments. The results show that within this time window (18-24 h), no significant change to cell concentration occurs.

EXAMPLE 5

Cell Sizes

To document the size range of *A. laidlawii* cultured in the serum-free medium according to the present invention, three different vials of frozen *A. laidlawii* stock were inoculated into separate flasks of GHB. Samples were incubated in GHB for 24 h at 37° C., 7% $CO_2$. Aliquots from each culture were prepared for scanning electron microscopy analysis, in which the size of the cells were measured. One way ANOVA, unstacked (95% confidence) was utilized to assess the three replicate cultures of *A. laidlawii* by length and separately by width. Results indicated that the cultures were not significantly different in length but exhibited significant difference in width. Other descriptive statistics of the sizing results are listed in the Table 4.

TABLE 4

Descriptive statistics of the sizing results

| Sample | n | Length (μm) | n | Width (μm) |
|---|---|---|---|---|
| Culture Rep 1 Mean and stdev | 50 | 0.402 ± 0.0997 | 50 | 0.368 ± 0.0734 |
| Culture Rep 2 1 Mean and stdev | 50 | 0.410 ± 0.0791 | 51 | 0.348 ± 0.0779 |
| Culture Rep 3 1 Mean and stdev | 50 | 0.393 ± 0.0701 | 51 | 0.406 ± 0.0793 |
| Overall Average | 150 | 0.402 | 152 | 0.374 |
| Overall Standard Deviation | 150 | ±0.0836 | 152 | ±0.0800 |
| Overall % CV | 150 | 20.8% | 150 | 21.4% |
| Overall Min | 150 | 0.271 | 152 | 0.1900 |
| Overall Max | 150 | 0.767 | 152 | 0.6420 |

EXAMPLE 6

Cell Aggregation

To demonstrate that *A. laidlawii* cultured in the serum-free medium according to the present invention are deaggregated and thus can distinguish among membranes with different bubble points, retention tests were performed using separate *A. laidlawii* cultures prepared in GHB. Culturing and enumeration were performed as described in Example 3. A number of membrane filters with different bubble points were tested. Bubble point is a commonly used indicator of pore size. It is based on the fact that, for a given fluid and pore size with a constant wetting, the pressure required to force an air bubble through the pore is inverse proportion to the size of the hole.

Figure 6:
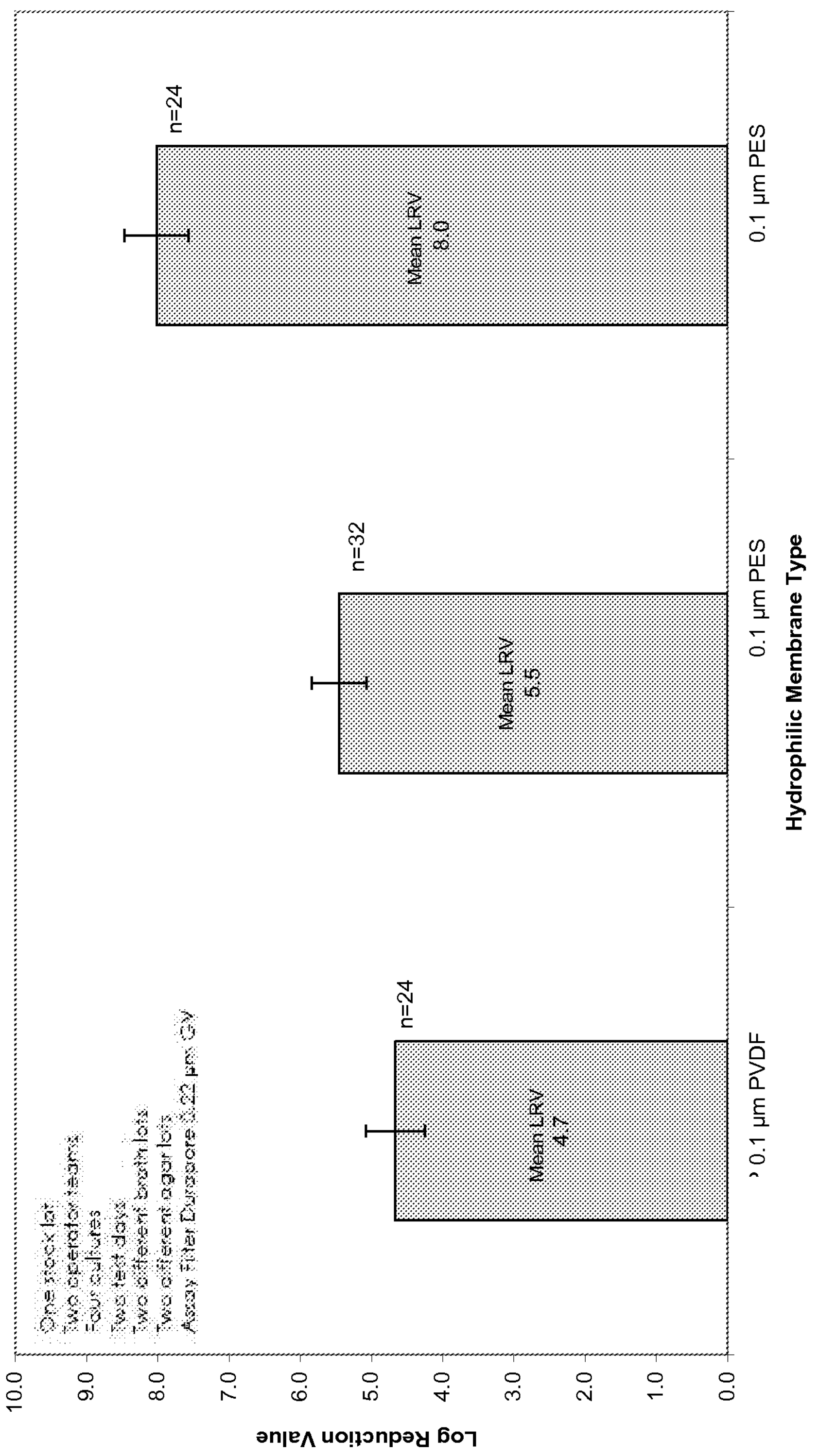
FIG. 6 is a bar graph showing log reduction values versus membrane type for *A. laidlawii* cultivated in the serum-free growth medium according to the present invention.

FIG. 6 illustrates log reduction versus membrane type for *A. laidlawii* cultivated in GHB. The results indicate that *A. laidlawii* cultivated in GHB was able to differentiate among membranes with different bubble points.

EXAMPLE 7

Media Aging

To demonstrate that GHB and GHA can consistently support growth of *A. laidlawii* for a minimum of 30 days from the date of preparation, media aging was tested. On day 0, two separate batches of GHB were prepared. Each batch contained a different set of manufacturers' lots of raw materials. The same two batches of the test medium were to be used throughout the length of study. Similarly, on day 0, two separate batches of GHA were prepared. Each batch contained a different set of manufacturers' lots of raw materials. The same two batches of the test medium were to be used throughout the study. On day 0, 2 flasks of each GHB batch were inoculated using *A. laidlawii* frozen stock. The same lot of *A. laidlawii* frozen stock was used throughout the study. The cultures were incubated and the cells enumerated as described in Example 3, to determine titer for media aging. One day 0, a sample of GHB and GHA was aseptically removed to determine pH of both media. On day 0, the same lot frozen *A. laidlawii* culture was defrosted and the thawed culture was plated using agar from each batch of GHA. (Culturing using GHB was not required because this assessment was also used to determine the titer of the frozen stock over time). The plates were incubated and the cells enumerated as described in Example 3, to determine titer for *A. laidlawii* frozen stocks. The determinations were repeated on Day 5, Day 10, Day 15, Day 20, Day 25, Day 30, Day 35 and Day 40 (±2 days to allow for weekends) from preparation of both GHB and GHA.

Figure 7:
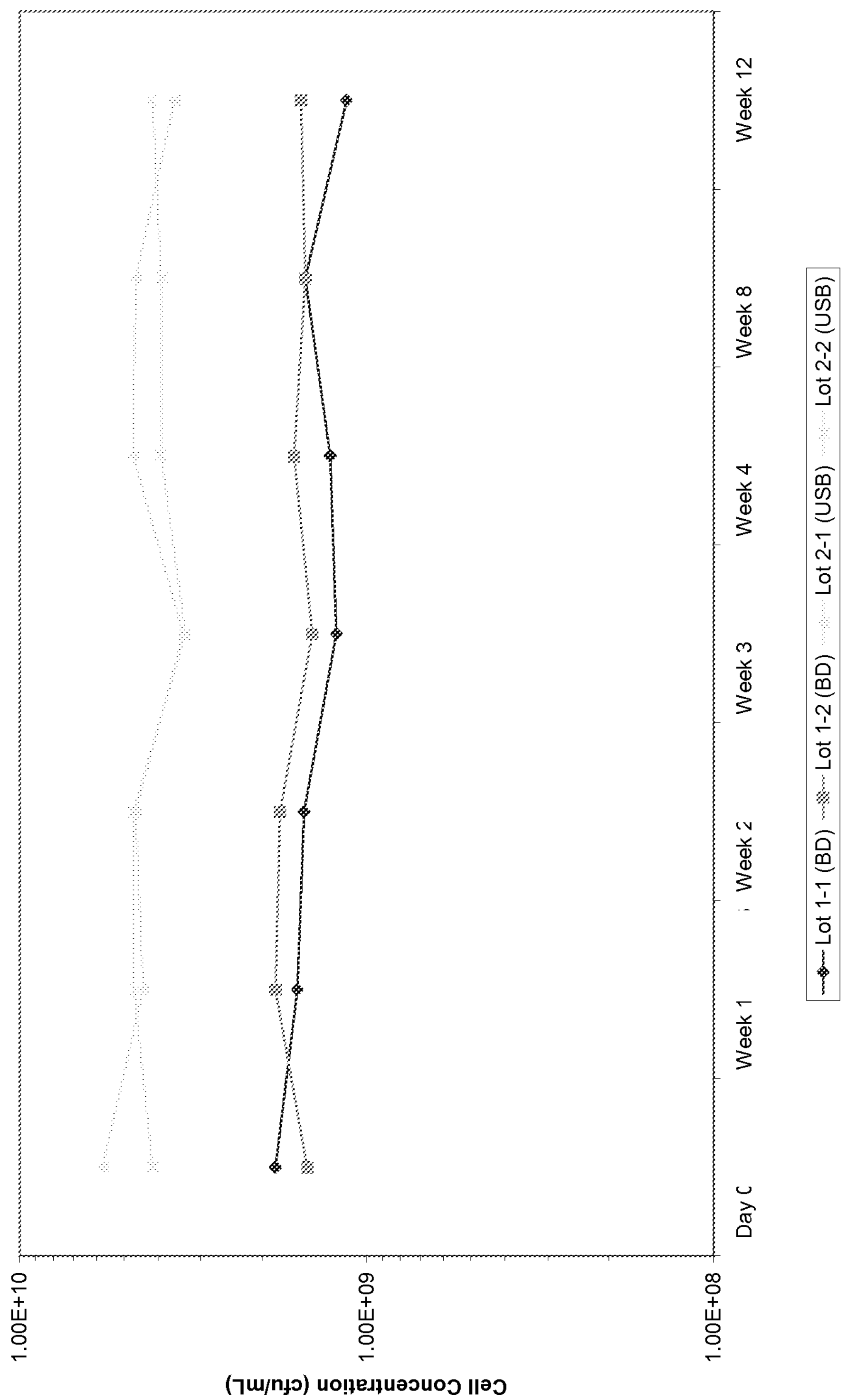
FIG. 7 is a graph showing cell concentration (cfu/mL) obtained from cultures grown in serum-free growth media with the hydrolysate component varied by vendor according to the present invention that have been stored for different lengths of time.
Figure 8:
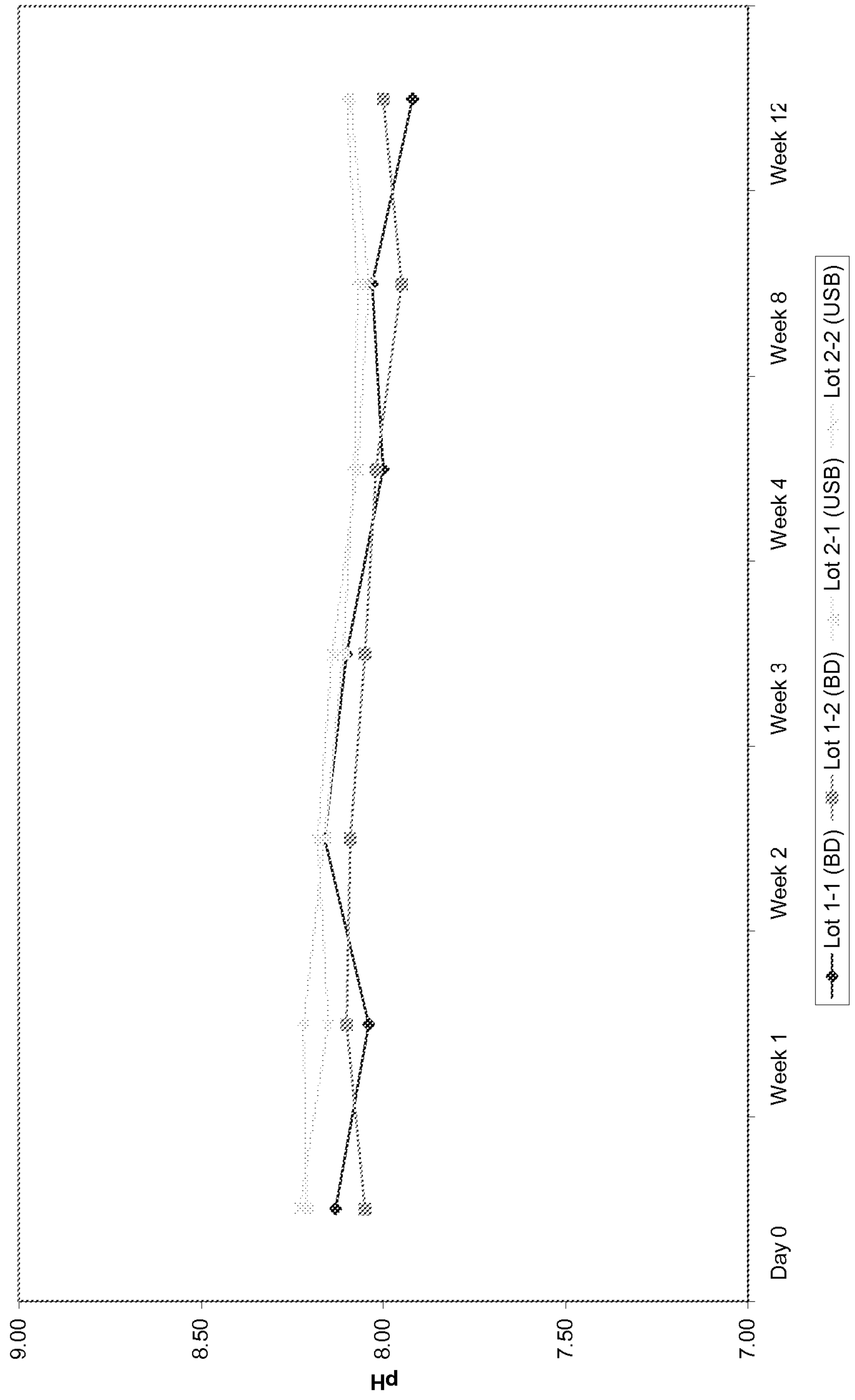
FIG. 8 is a graph showing pH of the serum-free growth media according to the present invention that have been stored for different lengths of time.

Two different vendors of polypeptone, one of the components of GHB, were examined in this study. FIG. 7 illustrates cell concentration of each culture of *A. laidlawii* ATCC 23206 grown in GHB stored over time with two different hydrolysate vendors, BD (Becton, Dickinson and Company, Franklin Lakes, N.J.) and USB (USB Corporation, Cleveland, Ohio). FIG. 8 illustrates pH of GHB stored over time with two different hydrolysate vendors, BD and USB. Even though there is a difference in cell counts between the two different vendors, titers of *A. laidlawii* within each batch did not drift more than 0.5 logs over the course of 30 days, and pH was within a range of 0.5 over the course of 30 days. As with any new lot of growth medium, a titer study should be conducted so that the challenge suspension can be diluted appropriately.

Figure 9:
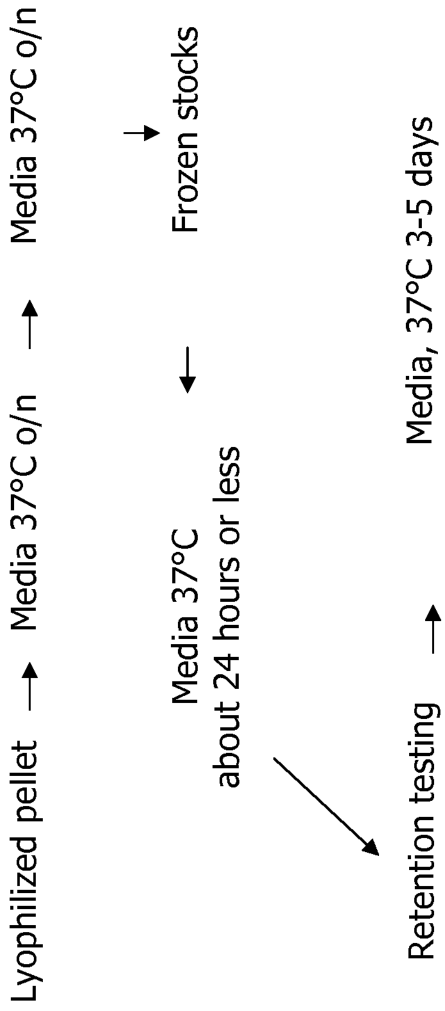
FIG. 9 is a flow-chart for growing *A. laidlawii* according to the present invention, wherein serum is omitted from all steps.

FIG. 9 depicts a flow-chart for growing and using *A. laidlawii* in retention testing 0.1 μM rated sterilizing grade filters according to the present invention, wherein serum is omitted from all steps. Time for incubation of *A. laidlawii* from a frozen stock to a high-titer culture ready for retention testing is reduced from two-step two days to one-step one day. The test filter can be challenged at a known level, preferably over $1.0\times10^9$ cfu/mL, with a cell culture more homogeneous in size. Time for incubation on agar-containing medium before enumeration of *A. laidlawii* in the filtrate is reduced from 5-6 days to 3-5 days. This shortened, simplified and consistent new procedure due to the use of serum-free media is able to produce similar LRVs as the procedure using serum-containing media.

While this invention has been particularly shown and described with references to example embodiments thereof, it will be understood by those skilled in the art that various changes in form and details may be made therein without departing from the scope of the invention encompassed by the appended claims.

What is claimed is:

1. A serum-free growth medium for cultivating or storing *Acholeplasma laidlawii* having a small, deaggregated and spherical morphology, comprising:
- (i) a nutrient selected from the group consisting of about 4% tryptose, about 4% polypeptone, and about 2% Mycoplasma Broth Base;
- (ii) bovine serum albumin ("BSA");
- (iii) one or more pH stabilizers;
- (iv) glucose; and
- (v) one or more fatty acids.

2. The serum-free growth medium of claim 1, wherein the medium comprises about 0.4% BSA.

3. The serum-free growth medium of claim 1, wherein the one or more pH stabilizers are selected from the group consisting of Tris, HEPES, and a combination thereof.

4. The serum-free growth medium of claim 3, wherein the medium comprises about 0.5% Trizma base.

5. The serum-free growth medium of claim 1, wherein the medium comprises about 0.7% glucose anhydrous.

6. The serum-free growth medium of claim 1, wherein the one or more fatty acids are selected from the group consisting of oleic, palmitic, myristic acids, and combinations thereof.

7. The serum-free growth medium of claim 6, wherein the one or more fatty acids are oleic acid and palmitic acid.

8. The serum-free growth medium of claim 7, where the medium comprises about 75 μM of oleic acid and about 75 μM of palmitic acid.

9. The serum-free growth medium of claim 1, further comprising about 1.2% agar.

10. The serum-free growth medium of claim 1, wherein the pH of the growth medium is adjusted to about 7.8.

11. The serum-free growth medium of claim 9, further comprising a chromogenic agent or dye selected from the group consisting of triphenyl tetrazolium chloride, Dienes stain and crystal violet.

12. The serum-free growth medium of claim 1, wherein the medium comprises:
- (i) a nutrient selected from the group consisting of about 4% tryptose, about 4% polypeptone, and about 2% Mycoplasma Broth Base;
- (ii) about 4% BSA;
- (iii) about 0.5% Trizma base;
- (iv) about 0.7% glucose anhydrous; and
- (v) about 75 μM of oleic acid and about 75 μM of palmitic acid.

13. The serum-free growth medium of claim 12, wherein the nutrient is about 4% tryptose.

14. The serum-free growth medium of claim 12, wherein the nutrient is 4% polypeptone.

15. The serum-free growth medium of claim 12, wherein the nutrient is 2% Mycoplasma Broth Base.

16. The serum-free growth medium of claim 12, further comprising about 1.2% agar.

17. The serum-free growth medium of claim 13, further comprising about 1.2% agar.

18. The serum-free growth medium of claim 14, further comprising about 1.2% agar.

19. The serum-free growth medium of claim 15, further comprising about 1.2% agar.

20. The serum-free growth medium of claim 12, wherein the pH of the growth medium is adjusted to about 7.8.

21. The serum-free growth medium of claim 16, further comprising a chromogenic agent or dye selected from the group consisting of triphenyl tetrazolium chloride, Dienes stain and crystal violet.

22. The serum-free growth medium of claim 17, further comprising a chromogenic agent or dye selected from the group consisting of triphenyl tetrazolium chloride, Dienes stain and crystal violet.

23. The serum-free growth medium of claim 18, further comprising a chromogenic agent or dye selected from the group consisting of triphenyl tetrazolium chloride, Dienes stain and crystal violet.

24. The serum-free growth medium of claim 19, further comprising a chromogenic agent or dye selected from the group consisting of triphenyl tetrazolium chloride, Dienes stain and crystal violet.

25. A serum-free growth medium for cultivating or storing *Acholeplasma laidlawii* having a small, deaggregated and spherical morphology, comprising:

(i) about 4% tryptose or about 4% polypeptone;

(ii) about 4% BSA;

(iii) about 0.5% Trizma base;

(iv) about 0.7% glucose anhydrous; and (v) about 75 μM of oleic acid and about 75 μM of palmitic acid.

26. A serum-free growth medium for cultivating or storing *Acholeplasma laidlawii* having a small, deaggregated and spherical morphology, comprising:

(i) about 2% Mycoplasma Broth Base;

(ii) about 4% BSA;

(iii) about 0.5% Trizma base;

(iv) about 0.7% glucose anhydrous; and (v) about 75 μM of oleic acid and about 75 μM of palmitic acid.

27. A serum-free growth medium for cultivating or storing *Acholeplasma laidlawii* having a small, deaggregated and spherical morphology, comprising:

(i) one or more nutrients consisting of about 4% tryptose, about 4% polypeptone, or about 2% Mycoplasma Broth Base;

(ii) bovine serum albumin ("BSA");

(iii) one or more pH stabilizers;

(iv) glucose; and (v) one or more fatty acids.

28. The serum-free growth medium of claim 27, wherein the medium comprises:

(i) one or more nutrients consisting of about 4% tryptose, about 4% polypeptone, or about 2% Mycoplasma Broth Base;

(ii) about 4% BSA;

(iii) about 0.5% Trizma base;

(iv) about 0.7% glucose anhydrous; and (v) about 75 μM of oleic acid and about 75 μM of palmitic acid.

* * * * *